Figure 1A:
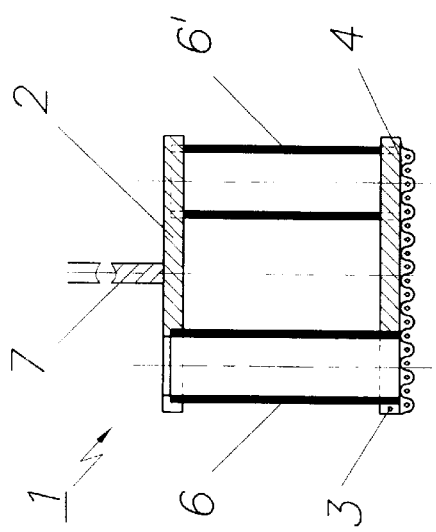

United States Patent
Löffler

[11] Patent Number: 6,163,149
[45] Date of Patent: Dec. 19, 2000

[54] DEVICE FOR DETERMINING THE DISSOLUTION TIME OF MEDICAMENTS IN PRESSED FORM, LIKE TABLETS, PILLS OR CAPSULES

[76] Inventor: Hans-Peter Löffler, Am Grundweg 20, 64342 Seeheim-Jugenheim, Germany

[21] Appl. No.: 09/051,575

[22] PCT Filed: Sep. 19, 1996

[86] PCT No.: PCT/DE96/01771

§ 371 Date: Apr. 6, 1998

§ 102(e) Date: Apr. 6, 1998

[87] PCT Pub. No.: WO97/14035

PCT Pub. Date: Apr. 17, 1997

[30] Foreign Application Priority Data

Oct. 6, 1995 [DE] Germany .......................... 195 37 179

[51] Int. Cl.[7] .......................... G01N 33/15; G01N 27/74
[52] U.S. Cl. .......................... 324/232; 73/866; 324/236
[58] Field of Search ............................ 324/232, 236; 73/866

[56] References Cited

U.S. PATENT DOCUMENTS 3,618,395  11/1971  Melliger .
4,754,657  7/1988  Schneider ................................. 73/866

FOREIGN PATENT DOCUMENTS 2530065   3/1977   Germany .
3325739   2/1984   Germany .
3414507   10/1985  Germany .
3520034   5/1986   Germany .
19719201  6/1998   Germany .
19739382  12/1998  Germany .

*Primary Examiner*—Thomas P. Noland

[57] ABSTRACT

The invention relates to a device for determining the dissolution time of medication in pressed form, like tablets and capsules, (especially to DAB 10, 3rd Supplement 1994, or the European Pharmacopoeia or USP [USA]), consisting of a frame (1) with a central column (7) and a base plate (3, 10) having a plurality of holes (5, 5', 11) covered from below by a mesh (4). Test tubes (6, 6') are arranged upright in said holes inside the frame (1). A disk (8, 15) can be movably inserted into said test tubes to weight the individual pressed medication. An electric coil (12) is disposed around each hole (11) and on and/or in the base plate (10), wherein the electric coil forms part of an electrical oscillation circuit (17). A conductor loop (16) is disposed on and/or in the disk (15) for damping the electrical oscillation circuit (17) depending on distance. The electric coil (12) and the conductor loop (16) together are connected to an electric supply and evaluation device (20, 23) to generate oscillations and evaluate the measurement results.

18 Claims, 4 Drawing Sheets

DEVICE FOR DETERMINING THE DISSOLUTION TIME OF MEDICAMENTS IN PRESSED FORM, LIKE TABLETS, PILLS OR CAPSULES

TECHNICAL FIELD

The invention relates to a device for determining the dissolution time of medicaments in pressed form, such as tablets, pills, or capsules, wherein the device comprises a frame with a center column and a base plate, wherein the base plate comprises a plurality of holes, wherein the holes are covered from below by a mesh, and wherein test tubes are arranged upright in the holes within the frame, wherein a disk is movably inserted into each test tube for weighting the individual medication, according to the preamble of claim 1.

STATE OF THE ART

The measurement of the dissolution time of medication in pressed form, such as tablets and capsules, is performed in a standardized testing set-up in order to assure the reproduceability of the measurement results (in particular to DAB 10, 3rd Supplement 1994 or European Pharmacopoeia or USP [USA]). It is determined based on the dissolution testing whether the tablets or capsules dissolve in a liquid medium within the prescribed time under precisely set-forth conditions. The main part of the apparatus comprises a rigid frame which contains six cylindrical test tubes made of glass. Each tube is provided with a cylindrical disk made of a transparent plastic material of a precisely specified relative density and size. The test tubes are supported in their upright position by an upper and a lower transparent plate made of plastic, wherein the plate comprises in each case six boreholes. All boreholes have the same distance from the center point and the same distance from one another. A mesh made of a stainless steel wire is disposed at the underside of the lower plate. A metal column is disposed such at the center of the plate that the apparatus can be suspended from the metal column in a suspension arrangement and can be uniformly moved upward and downward by 50 to 60 mm with a motor 28 to 32 times per minute. For this purpose, the apparatus is suspended in a suitable container comprising the prescribed liquid. After filling one tablet or capsule into each tube and weighting the tube with the disk, the determination of the dissolution time of the tablets or capsules is performed by observation of the measurement device and time-keeping by the operating person.

A dissolution device for test bodies, in particular tablets, is known from the German printed patent document DE 35 20 034 C1, wherein the test bodies are disposed in containers of a dissolution basket between a Hall generator and a disk provided with a magnet. The containers of the dissolution basket are heated with a heating installation to a constant temperature. Once the test body dissolves, the disk moves together with the magnet toward the Hall generator such that the Hall generator emits a signal, wherein the signal can be fed to and displayed on a recording device upon exceeding of a sound threshold. The transmission of the energy for the electrical circuits in the dissolution basket occurs through contacts or with a high-frequency transmitter arid a high-frequency receiver. The transmission of the signals to the recording device is performed with optoelectronic components.

An automatic dissolution-time measurement device for the pharmaceutical quality control and production control of tablets and dragées or coated tablets in a conductive test liquid is known from the German printed patent document DE 94 19 245 U1, wherein the measurement device comprises a basket-like frame disposed in a beaker with a plurality of glass tubes disposed in the frame. The bases of the glass tubes are formed by circular sieve or mesh bottom plates as supporting bottom faces for the glass tubes. Each mesh bottom plate is comprised of two current-carrying, electrode-forming wire-mesh halves, wherein the wire-mesh halves are disposed at a spacing from one another thereby forming a slot in between. A test sample is disposed in each glass tube. The test sample is covered with a floating body or floater which rests on the test sample. The floater exhibits at its underside an embedded contact framework made of a metallic material. The conductivity of the test liquid changes upon motion of the beaker and dissolution of the tablets, wherein the conductivity can be measured between the wire-mesh halves and the contact framework.

A tablet-disintegration time measurement device with agitated tubes in a bath liquid is known from the U.S. printed patent document 3,618,395. This measurement device includes a plurality of opposed, spaced electrodes at the base of the tablet-containing tubes. The presence of a tablet disturbs an electromagnetic field set up at the electrodes, wherein the disturbance actuates a timer, and wherein the signals of the timer can be evaluated.

Previous attempts for a fully automatic measurement always resulted in inadmissible changes of the test apparatus. Such changes are however only admissible to a very small degree according to DAB 10.

Technical Object

It is an object of the invention to provide for a device of the initially recited kind, which device captures in a contactless way the motion of the disks within the device without changing the prescribed parameters for the apparatus according to DAB 10, and which device is to determine continuously the decreasing thickness or the residual thickness of the medication in pressed form such as tablets, pills, or capsules during the dissolution process. In addition, the disks and the frames are to be interchangeable without having to carry out a new calibration of the device; as in the past, the disks and frames are to be easy to clean, without thereby influencing the measurement system.

Disclosure of the Invention and its Advantages

The solution of the object lies according to the invention in that an electric coil is disposed around each hole on and/or in the base plate of the frame, wherein the electric coil forms part of an electrical oscillation circuit. A conductor loop is disposed on and/or in the disk for path-dependently damping the electrical oscillation circuit. The electric coil and the conductor loop are jointly connected to an electric supply device and an electric evaluation device to generate oscillations and to evaluate the measurement results.

Normally, the residual thickness is preset as set value. When the actual value of the medication is less than the residual thickness, then it is deemed that the medication is dissolved.

The device is structured in an advantageous way such that the geometry and the density of the disks as well as the geometry of the test tubes and the structure of the mesh base of the frame remain unchanged. In addition, the disks and the frames are interchangeable without requiring a new calibration of the device.

In an advantageous way, the coil can be formed as single-layer coil or as multi-layer coil on a separate coil support, wherein the coil support is either resting on the base plate of the frame, or is integrated into the base plate of the frame, or is identical with the base plate of the frame. Each coil can be a flat coil, wherein one half of the windings of the flat coil are integrated into the upper side and the other half into the underside of the base plate or, respectively, the coil support. The lines to the coils are formed congruent relative to the upper side and underside of the base plate or, respectively, of the coil support. In addition, the coils can be disposed in multi-layer technique on a multi-layer plate serving as a base plate or, respectively, as a coil support, and the coils can also be disposed within a coil base or, respectively, coil support separated from the base plate of the frame.

A mutual influencing of the measuring points or, respectively, of the oscillation circuits is avoided in that the electrical oscillation circuits are controllable with a multiplexer, wherein the multiplexer in each case energizes only one oscillation circuit.

The energy supply and the data transfer is performed preferably contactless by means of a magnetic field between the frame and a drive unit, wherein the frame is supported within the drive unit with the center column.

In addition, the electric coupling path can in each case be comprised of one half of a pot core or shell-type core with inserted coil on each side, wherein on the driving side the shell-type core half with coil is integrated into the support for the frame or, respectively, for the center column, and on the side of the frame the shell-type core half with coil is integrated into the center column.

The sensors comprised of oscillation circuits, evaluation device as well as inductive energy coupling and data coupling can preferably be switched to a common bus and receive a bus address, wherein a transport address is inserted into the message to be delivered for the parallel operation of the sensors at the bus. The transmitter and receiver coils of the sensors for coupling to the driving unit can be operated with differing frequencies for the separation of the energy and data flow.

A change of the density of the disks by the insertion of the conductor loop is compensated for by a hollow space in the interior of the disk, if it should be necessary.

The oscillation circuit coils are advantageously formed by conductor paths within the base plate, wherein the conductor paths surround the respective test tubes. The spatial expansion of the field is limited based on the small length of the coils such that an influencing of the oscillation circuit by the mesh bottom plates of the frame is small. A mutual influencing of the measuring points is prevented with the use of the multiplexer.

Figure 2:
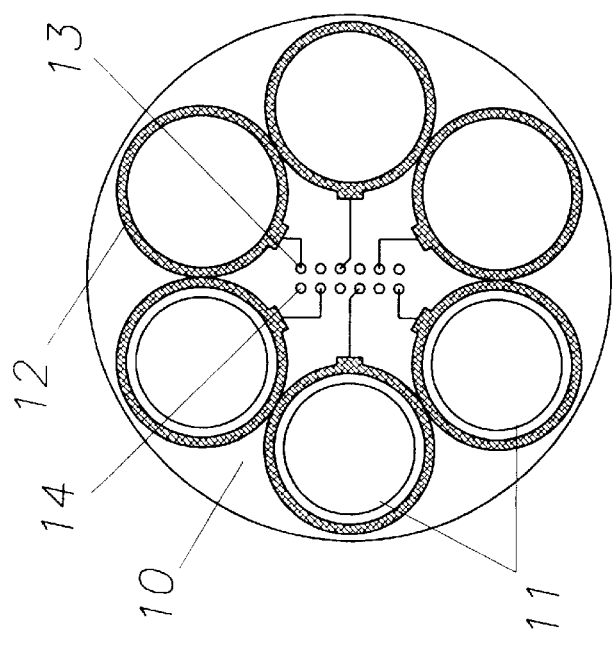
Figure 3:
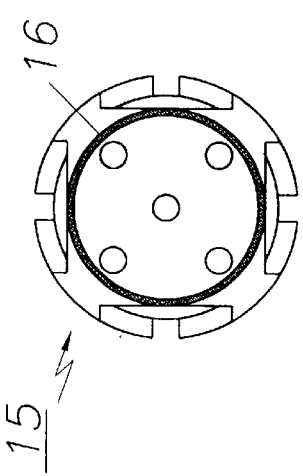
Figure 4:
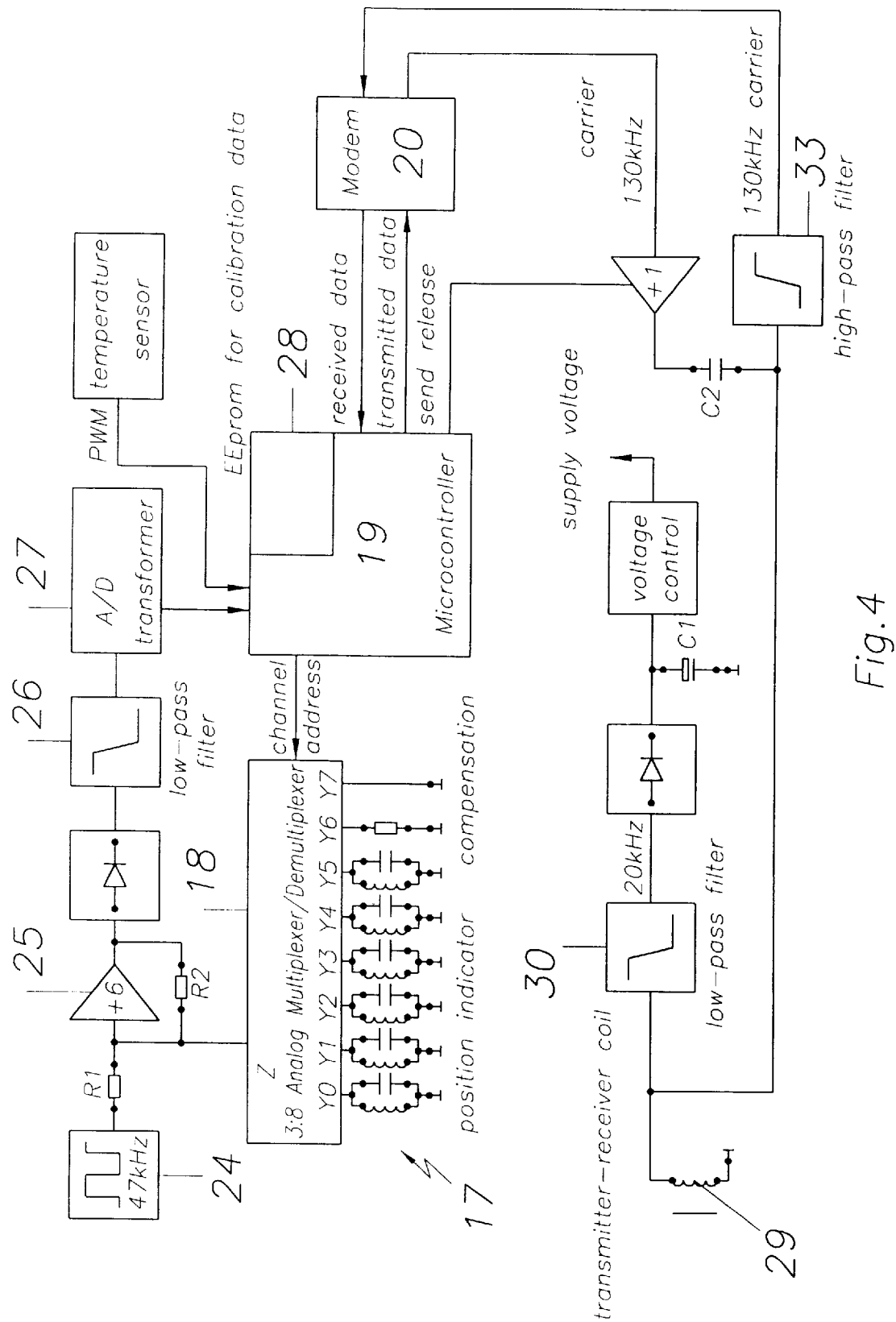
Figure 5:
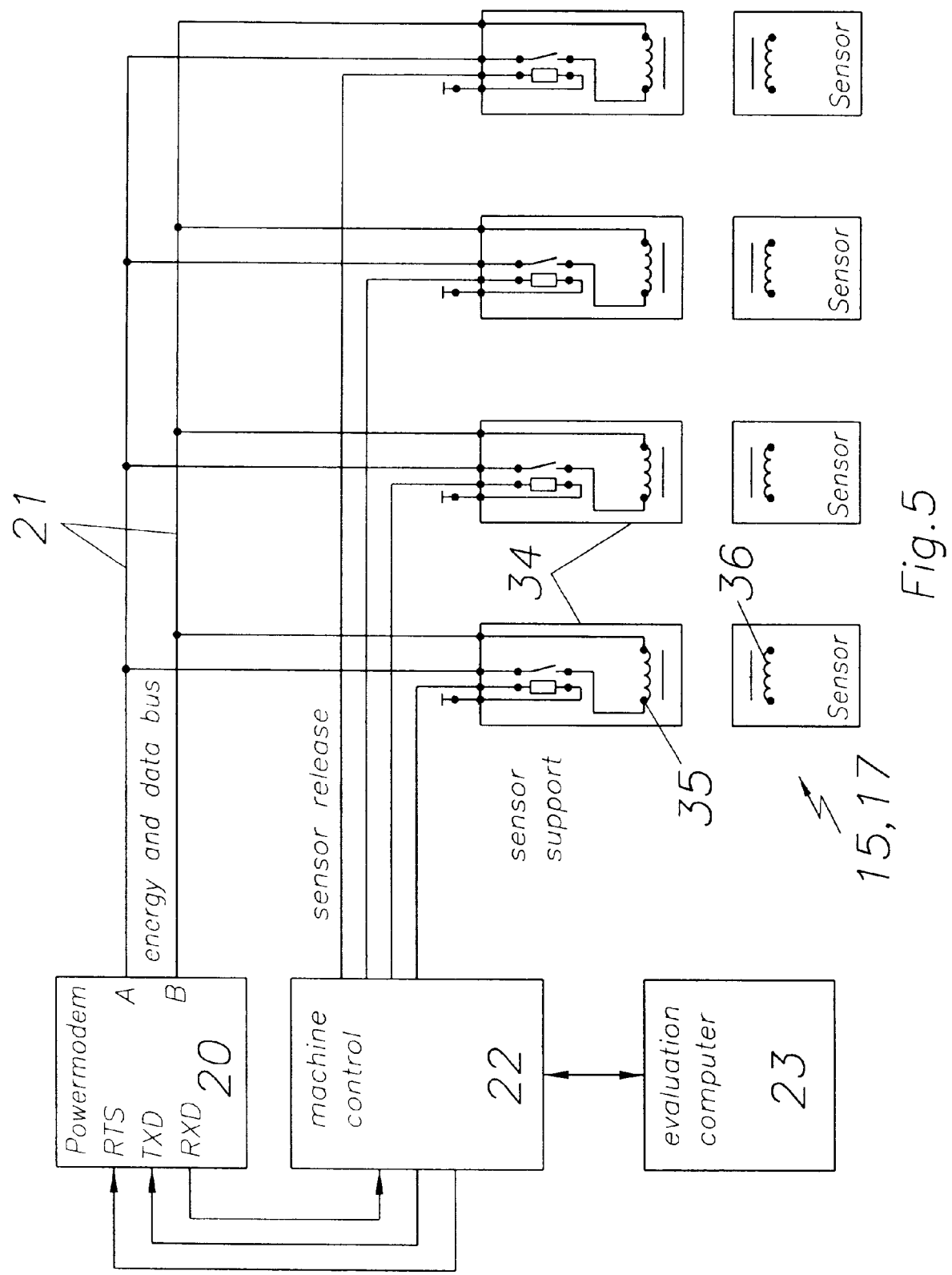
Figure 6:
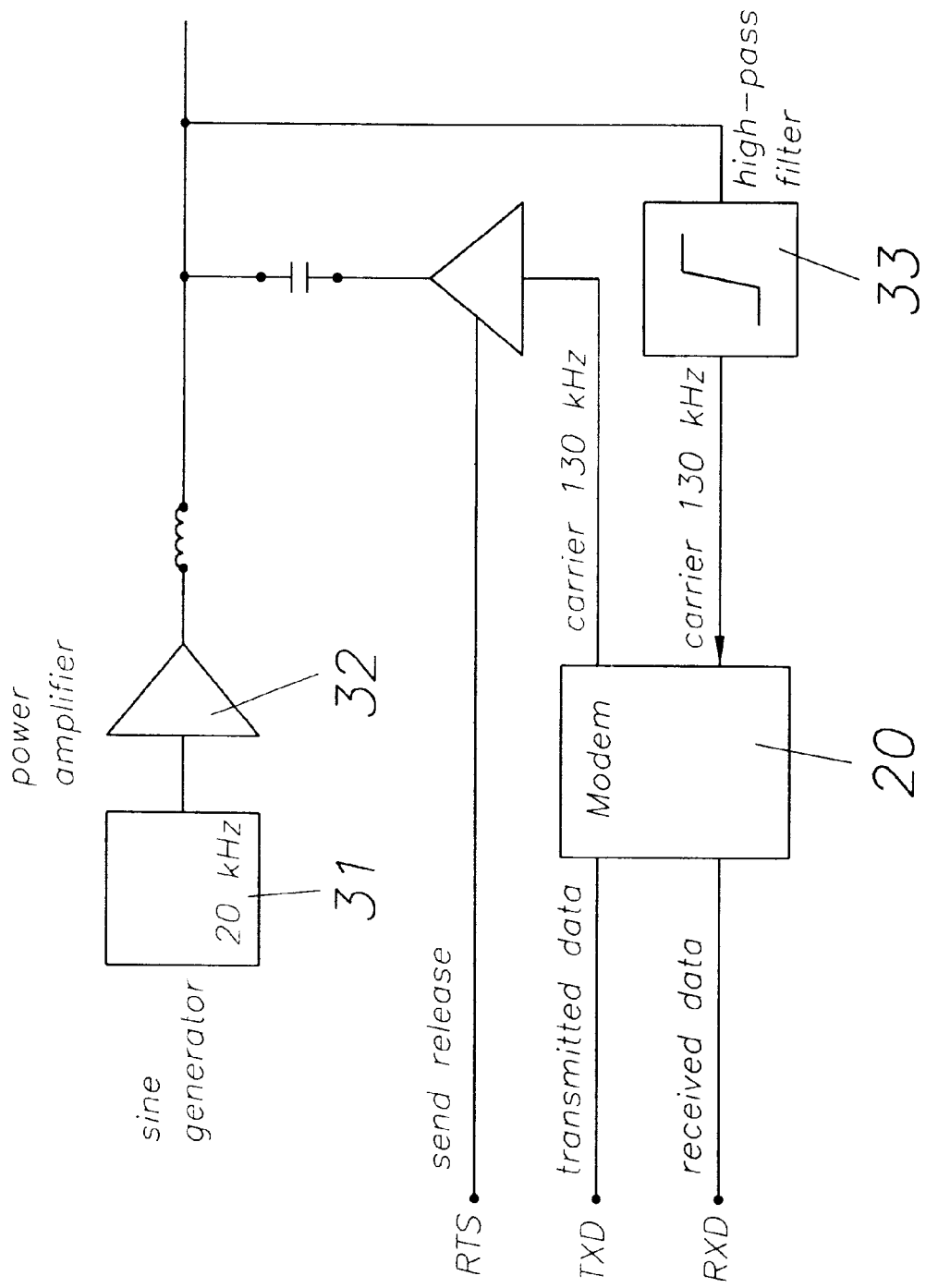

Short description of the drawing, in which is shown:

FIGS. 1 a, b, c a device of the state of the art according to DAB 10;

FIG. 2 a base plate including holes for the insertion of the test tubes, wherein coils are formed around the holes on the base plate for the formation of oscillation circuits;

FIG. 3 a disk, as it is inserted into each test tube;

FIG. 4 a block diagram of the electric part of the device;

FIG. 5 a block diagram of a complete system with four devices or sensors connected to a bus; and FIG. 6 a block diagram of the power modem.

PATHS TO THE EXECUTION OF THE INVENTION

Figure 1B:
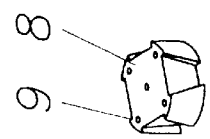
Figure 1C:
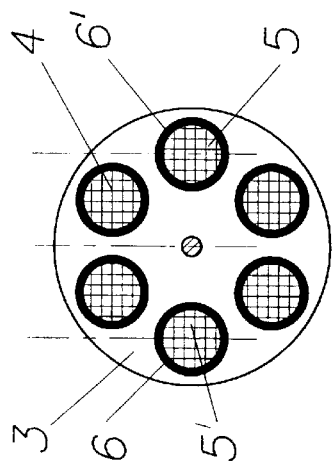

FIGS. 1a, 1b, 1c show a device according to DAB 10, Nov. 3, 1994. The device comprises a frame 1 with a center column 7 as well as a circular cover plate 2 and a base plate 3. The cover plate 2 and the base plate 3 exhibit a plurality of holes 5, 5' and, as a rule, six holes. Test tubes 6, 6' made of glass are disposed in the holes 5, 5'. The base plate 3 is covered at its underside with a mesh 4 made of stainless steel wire. The plates 2, 3 are rigidly separated from one another by vertical metal rods, not shown, at the outer side of the frame 1. For the dissolution testing, in each case one tablet or capsule are placed into each test tube 6, 6', and a disk 8, having precisely defined recesses 9, is placed onto the tablet or capsule to weight the tablet or capsule, and the dissolution time is measured.

The mechanical modification of the parts which are changed relative to the apparatus according to DAB 10 is shown in FIGS. 2 and 3.

Holes 11 are disposed on a base plate 10, corresponding to the base plate 3 of FIG. 1, wherein the holes 11 have the same distance from the center point of the base plate 10 as well as the same distance from each other. A coil 12 is disposed around each hole 11, wherein the winding ends lead to contacts 13, 14. Thus, the base plate forms the coil support 10. The coils 12 are integrated into the base plate. The coil support 10 can however also be formed as an intermediate base plate.

Each one of the coils is formed as a flat coil 12, wherein one half of the windings of the flat coil are integrated into the upper side and the other half into the underside or bottom of the base plate 10. The lines 13, 14 to the coils are formed congruent relative to the upper side and the underside of the base plate 10. The winding ends 13, 14 lead above and below the base plate to contact pins of a plug according to FIG. 2. The lines are guided upwardly in the center column 7.

A conductor loop 16 is disposed on a surface of a disk 15 or is integrated into the disk 15, wherein the disk corresponds in its dimensions and its density to the disk 8 according to DAB 10.

According to FIG. 4, the coils 12 are in each case part of LC oscillation circuits 17, wherein the coils 12 are excited and energized with a square-wave generator 24 via an analog multiplexer 18. The individual oscillation circuit is path-dependently dampened with the conductor loop 16, disposed in the disk 15. Since the resonance frequency of the oscillation circuit 17 is selected much higher than the exciter frequency of the square-wave generator 24, a decaying oscillation of the oscillation circuit 17 occurs after each slope of the exciter signal. The stronger the damping of the oscillation circuit 17, the faster the oscillations decay. Thereby, the area of the envelope represents a measure for the damping of the oscillation circuit 17. The realization of the capturing of the values to be measured is performed by feeding the square-wave voltage of the square-wave generator 24 with the analog multiplexer 18 to the LC oscillation circuit 17 of the device. The voltage, resulting within the oscillation circuit 17, is again fed with the multiplexer 18 to an amplifier 25. The inherent losses of the oscillation circuit 17 can in part be compensated for with a positive feedback of the amplifier output to the input.

The determination of the envelope area of the oscillation circuit voltage occurs by rectification and subsequent low-pass filtering 26 of the amplified oscillation circuit voltage. The output voltage of the low-pass filter 26 is fed to a analog/digital A/D transformer 27, wherein the output signal of the transformer 27 is sent to a microcontroller 19. The microcontroller calculates the distance of the corresponding disk 15 to the base of the frame 1 from the voltage values received. Correction factors can be automatically determined by the software of the microcontroller 19 in a calibration process and stored in a non-volatile memory storage 28, wherein the non-volatile memory storage 28 is preferably an EEprom.

The distance values are continuously recorded during the dissolution-time determination of the tablets or capsules and are transmitted based on an inductive coupling path to an evaluation computer 23, FIG. 5.

According to FIG. 5, the energy supply and data transfer between the frame 1 and the evaluation device 23 is preferably performed contactless by a magnetic field. For this purpose, the electric coupling path is comprised in each case of one half of a pot core with an inserted coil 35 on the side of the sensor support 34, i.e. the driving side for the frame, as well as of a pot core half with the coil 36 on the sensor side. The pot core and the coil 35 are integrated into the sensor support 34 in the support for the frame. The shell-type-core half and the coil 36 are integrated into the center column of the respective frame on the side of the frame 1 or, respectively, of the sensor.

The energy transfer and the data transfer to the coils 12 can occur simultaneously through the coupling-coil path 35-36 at different frequencies, whereby a separation of the energy transfer and data transfer is possible with a filter. The energy transfer is performed by applying a 20-kHz alternating voltage of a sine generator 31 to the primary side of a transmitter-receiver coil 29 of the coupling path or, respectively, of the transmitter. The secondary-induced voltage is rectified and stabilized behind a low-pass filter 30 for the separation of the data signal.

In addition, the connection of the sensor supports 34 to the energy and data bus 21 can be seen on FIG. 5. The sensors comprise in each case an oscillation circuit 17, an evaluation device 20, 23, as well as an inductive energy and data coupling by means of the coupling-coil path 35-36 and the sensors are switched to a common bus 21 and can receive a bus address. For this purpose, a transport address is inserted into the message to be delivered.

The data transfer can be performed according to FIGS. 5 and 6 by way of a half-duplex operation with a modem 20 on each side of the coupling path. The respective data transmitter modulates a carrier frequency, preferably in AM or in FSK, of 130 kHz and switches the signal with a power amplifier 32 to the winding of the transmitter. The receiver side feeds the output voltage of the transmitter through a high-pass filter 33 to the input of the modem 20. The modem demodulates the signal and wins back the bit current of the transmitter.

The parallel operation of several devices or, respectively, frames is possible with one power modem 20 based on the insertion of the transport address into the messages. The devices are initially individually connected to the bus 21 and receive a bus address. The parallel operation at the bus occurs once all devices have received an address.

Industrial Applicability

The device is employed in particular for determining the dissolution time of medication in pressed form according to "Deutsches Arzneibuch" DAB, European Pharmacopoeia or United States Pharmacopoeia USP. The usefulness and the advantages of the invention reside in particular in that a contactless and continuous recording of the motion of the disks and thus the dissolution of the medication in pressed form, such as tablets, pills, or capsules, within the test tubes is possible according to the invention, in order to determine electrically the current thickness of the medication from these recordings during the dissolution process and the dissolution time.

| List of Reference Numerals: | |
|---|---|
| 1 | Frame |
| 2 | Cover plate |
| 3 | Base plate |
| 4 | Mesh |
| 5, 5' | Holes |
| 6, 6' | Test tubes |
| 7 | Center axle or column |
| 8 | Disk |
| 9 | Recesses |
| 10 | Coil support or base plate |
| 11 | Holes |
| 12 | Coils |
| 13, 14 | Contacts |
| 15 | Disk |
| 16 | Conductor loop |
| 17 | Oscillation circuits |
| 18 | Multiplexer |
| 19 | Microcontroller |
| 20 | Modem or, respectively, power modem |
| 21 | Bus |
| 22 | Machine control |
| 23 | Evaluation computer |
| 24 | Square-wave generator |
| 25, 32 | Amplifier |
| 26 | Low-pass filter |
| 27 | A/D transformer |
| 28 | Non-volatile memory storage |
| 29 | Transmitter-receiver coil |
| 30 | Low-pass filter |
| 31 | Sine generator |
| 33 | High-pass filter |
| 34 | Sensor supports |
| 35, 36 | coupling coils or coupling-coil path |

What is claimed is:

1. A device for determining the dissolution time of medications in pressed form comprising a frame;

a center column furnished at the frame;

a base plate furnished at the frame, wherein the base plate is furnished with a plurality of holes;

a mesh covering the holes from below, test tubes placed upright in the holes and located within the frame, a plurality of disks, with each of the disks insertable into each one of the test tubes for loading and weighting the individual medications, a plurality of electric coils, with each one of the electric coils disposed around a corresponding one of the holes, wherein each electric coil forms part of one of a plurality of electrical oscillation circuits, a plurality of conductor loops, with each conductor loop disposed near a corresponding one of the plurality of disks for path-dependently damping the electrical oscillation circuits, wherein each electric coil and each conductor loop are connected to an electric power supply to generate oscillations and to an evaluation device for evaluating measurement results.

2. The device according to claim 1, wherein each one of the plurality of electric coils is formed as a single-layer coil.

3. The device according to claim 1, wherein each one of the plurality of electric coils is formed as a multi-layer coil.

4. The device according to claim 1, further comprising
a coil support, wherein each electric coil is a flat coil having windings, wherein a first half of the windings of the flat coil are integrated into an upper side and a second half into a bottom side of the coil support, and wherein feed lines to the electric coils are formed congruent relative to the upper side and the bottom side of the coil support.

5. The device according to claim 1, further comprising
a coil support, wherein each electric coil is a flat coil having windings, wherein a first half of the windings of the flat coil are integrated into an upper side and a second half into a bottom side of the base plate of the frame, and wherein feed lines to the electric coils are formed congruent relative to the upper side and the bottom side of the base plate.

6. The device according to claim 1, further comprising
a multi-layer plate, wherein the electric coils are disposed in multi-layer technique on the multi-layer plate.

7. The device according to claim 1, wherein the electric coils are disposed separated from the base plate of the frame.

8. The device according to claim 1, further comprising
a multiplexer connected to the electrical oscillation circuits, wherein the electrical oscillation circuits are controllable with the multiplexer.

9. The device according to claim 1, further comprising
a drive unit;
a source of a magnetic field disposed between the frame and the drive unit, wherein an energy supply and a data transfer is performed contactless by means of a magnetic field between the frame and a drive unit, wherein the frame is supported with the center column disposed within the drive unit.

10. The device according to claim 9, further comprising
a plurality of pot cores, wherein an electric coupling path is in each case comprised of one half of a corresponding one of the plurality of pot cores having a respective electric coil inserted on each side, wherein a first pot-core half with electric coil disposed on a driving side is integrated into a support for the center column, and on a side of the frame a second pot-core half with electric coil is integrated into the center column.

11. The device according to claim 9, further comprising
a plurality of pot cores, wherein an electric coupling path is in each case comprised of one half of a corresponding one of the plurality of pot cores; having a respective electric coil inserted on each side, wherein a first pot-core half with electric coil disposed on a driving side is integrated into a support for the frame, and on a side of the frame a second pot-core half with electric coil is integrated into the center column.

12. The device according to claim 1, further comprising
a common bus;
a plurality of frames each comprised of an oscillation circuit, an evaluation device, and an inductive energy coupling and a data coupling, are switched to the common bus and receive a bus address, and wherein a transport address is inserted into a message to be delivered for a parallel operation of the frames at the common bus.

13. The device according to claim 1, further comprising
a common bus;
a plurality of sensors each comprised of an oscillation circuit, an evaluation device, and an inductive energy coupling and a data coupling, are switched to the common bus and receive a bus address, and wherein a transport address is inserted into a message to be delivered for a parallel operation of the sensors at the common bus.

14. The device according to claim 13, wherein each oscillation circuit includes a transmitter coil and a receiver coil, wherein the transmitter coils and the receiver coils of the sensors for coupling to a driving side of the frames are operated with differing frequencies for a separation of an energy flow and a data flow.

15. A method for determining the dissolution time of medication in pressed form comprising
connecting a plurality of electric coils and a plurality of conductor loops to an electric power supply;
placing a medication in pressed form into each one of a plurality of test tubes, wherein the test tubes are located in a frame, wherein a center column is furnished at the frame, and wherein a base plate is furnished at the frame, wherein the base plate is furnished with a plurality of holes, wherein a mesh is covering the holes from below, and wherein the test tubes are placed upright in the holes and located within the frame;
inserting each one of a plurality of disks into each one of the test tubes for loading and weighting the individual medications;
energizing the plurality of electric coils, wherein each one of the electric coils is disposed around a corresponding one of the holes, and wherein each electric coil forms part of an electrical oscillation circuit;
damping the electrical oscillation circuit with a plurality of conductor loops, wherein each conductor loop is disposed on a corresponding one of the plurality of disks for path-dependently damping the electrical oscillation circuit;
generating oscillations in each electric coil and in each conductor loop with power furnished by the electric power supply;
feeding the oscillations to an evaluation device for evaluating the measurement of the dissolution time of the medication.

16. A method for determining the dissolution time of medication in pressed form comprising
connecting a plurality of electric coils and a plurality of conductor loops to an electric power supply;
placing a medication in pressed form into each one of a plurality of test tubes, wherein the test tubes are located in a frame, wherein a center column is furnished at the frame, and wherein a base plate is furnished at the frame, wherein the base plate is furnished with a plurality of holes, wherein a mesh is covering the holes from below, and wherein the test tubes are placed upright in the holes and located within the frame;
inserting each one of a plurality of disks into each one of the test tubes for loading and weighting the individual medications;
energizing the plurality of electric coils, wherein each one of the electric coils is disposed around a corresponding one in the base plate, and wherein each electric coil forms part of an electrical oscillation circuit;
damping the electrical oscillation circuit with a plurality of conductor loops, wherein each conductor loop is disposed on a corresponding one of the plurality of disks for path-dependently damping the electrical oscillation circuit;
generating oscillations in each electric coil and in each conductor loop with power furnished by the electric power supply;
feeding the oscillations to an evaluation device for evaluating the measurement of the dissolution time of the medication.

17. A method for determining the dissolution time of medication in pressed form comprising connecting a plurality of electric coils and a plurality of conductor loops to an electric power supply;

placing a medication in pressed form into each one of a plurality of test tubes, wherein the test tubes are located in a frame, wherein a center column is furnished at the frame, and wherein a base plate is furnished at the frame, wherein the base plate is furnished with a plurality of holes, wherein a mesh is covering the holes from below, and wherein the test tubes are placed upright in the holes and located within the frame;

inserting each one of a plurality of disks into each one of the test tubes for loading and weighting the individual medications;

energizing the plurality of electric coils, wherein each one of the electric coils is disposed around a corresponding in the base plate, and wherein each electric coil forms part of an electrical oscillation circuit;

damping the electrical oscillation circuit with a plurality of conductor loops, wherein each conductor loop is disposed in a corresponding one of the plurality of disks for path-dependently damping the electrical oscillation circuit;

generating oscillations in each electric coil and in each conductor loop with power furnished by the electric power supply;

feeding the oscillations to an evaluation device for evaluating the measurement of the dissolution time of the medication.

18. A method for determining the dissolution time of medication in pressed form comprising connecting a plurality of electric coils and a plurality of conductor loops to an electric power supply;

placing a medication in pressed form into each one of a plurality of test tubes, wherein the test tubes are located in a frame, wherein a center column is furnished at the frame, and wherein a base plate is furnished at the frame, wherein the base plate is furnished with a plurality of holes, wherein a mesh is covering the holes from below, and wherein the test tubes are placed upright in the holes and located within the frame;

inserting each one of a plurality of disks into each one of the test tubes for loading and weighting the individual medications;

energizing the plurality of electric coils, wherein each one of the electric coils is disposed around a corresponding one of the holes, and wherein each electric coil forms part of an electrical oscillation circuit;

damping the electrical oscillation circuit with a plurality of conductor loops, wherein each conductor loop is disposed in a corresponding one of the plurality of disks for path-dependently damping the electrical oscillation circuit;

generating oscillations in each electric coil and in each conductor loop with power furnished by the electric power supply;

feeding the oscillations to an evaluation device for evaluating the measurement of the dissolution time of the medication.

* * * * *